(12) United States Patent
Han

(10) Patent No.: US 8,536,322 B2
(45) Date of Patent: Sep. 17, 2013

(54) METHOD FOR NUCLEIC ACID ISOLATION BY SOLID PHASE REVERSIBLE BINDING OF NUCLEIC ACIDS

(75) Inventor: Zhiqiang Han, Lexington, MA (US)

(73) Assignee: Zhiqiang Han, Lexington, MA (US)

( * ) Notice: Subject to any disclaimer, the term of this patent is extended or adjusted under 35 U.S.C. 154(b) by 193 days.

(21) Appl. No.: 12/906,969

(22) Filed: Oct. 18, 2010

(65) Prior Publication Data

US 2011/0172409 A1    Jul. 14, 2011

Related U.S. Application Data

(60) Provisional application No. 61/279,158, filed on Oct. 19, 2009.

(51) Int. Cl.
*C07H 21/00* (2006.01)
(52) U.S. Cl.
USPC ............... 536/25.4; 536/25.41; 536/25.42
(58) Field of Classification Search
None
See application file for complete search history.

(56) References Cited

U.S. PATENT DOCUMENTS

| | | | | |
|---|---|---|---|---|
| 5,523,231 A | * | 6/1996 | Reeve | 435/270 |
| 5,705,628 A | * | 1/1998 | Hawkins | 536/25.4 |
| 7,393,698 B2 | * | 7/2008 | Furukawa et al. | 436/526 |

* cited by examiner

*Primary Examiner* — Patrick Lewis
(74) *Attorney, Agent, or Firm* — Duan Wu, Esq.; Milstein, Zhang & Wu

(57) ABSTRACT

The invention includes a method for separating polynucleotides, such as DNA, RNA and PNA, from a solution containing polynucleotides by reversibly and non-specifically binding the polynucleotides to a solid surface having a functional amide group-coated surface. The materials containing a solid surface can be in the form of microparticles, fibers, beads, membranes, test tubes, pipette tips or microwells and can further comprise a magnetic core portion. The pH, salt and concentration of crowding reagent, such as polyethylene glycol or alcohol, of the solution is adjusted to levels which result in nucleic acid binding to the solid surface. The magnetic microparticles with bound polynucleotides are separated from the solution under mild alkaline conditions and the nucleic acids are eluted from the magnetic microparticles. Solutions having different nucleic acid concentrations can be normalized by restricting the availability of the solid phase surface.

27 Claims, 3 Drawing Sheets

1. 5 ul PCR product
2. 10 ul PCR product
3. 15 ul PCR product
4. 20 ul PCR product

METHOD FOR NUCLEIC ACID ISOLATION BY SOLID PHASE REVERSIBLE BINDING OF NUCLEIC ACIDS

This patent application claims the priority date of the provisional patent application with application number U.S. 61/279,158 filed on Oct. 19, 2009.

BACKGROUND OF THE INVENTION

Preparation and manipulation of nucleic acids are critical steps for molecular biology, genetic studies and diagnostics. Although there are many existing methods for nucleic acids isolation and manipulation, they have one or more limitations. The limitations include requiring the use of hazardous chemicals, requiring extra drying steps, being difficult to automate, resulting in nucleic acids solution containing contaminants, causing DNA denaturation or not cost effective, etc. Other limitations include low yield, binding quantification and analysis. Some of the methods and limitations have been described in U.S. Pat. Nos. 5,523,231, 5,705,628 and 7,022,835 and WO/1984/001503. Some of the limitations have also been described in publication by Jan Kieleczawa, "DNA Sequencing II: Optimizing the Isolation, Preparation and Clean-up" 127-163. These limitations have restricted the application of the underlying methods.

The present invention was to provide a method for reversible immobilizing/binding and purifying nucleic acids as well as normalizing nucleic acids respectively, which at least partially avoids the limitations and which enables fast purification and normalization of a large number of samples.

SUMMARY OF THE INVENTION

It is the objects of the present invention to provide methods for immobilizing/binding and purifying nucleic acids, which at least partially avoid the disadvantages of the methods known in the prior art and which in particular enables a simple and cost-effective purification of a large number of samples. It is another object to provide a method using amide functional group for binding nucleic acids non-specifically and reversibly to solid phase materials. It is another object to provide methods for binding and releasing nucleic acids from the solid phase materials without relying on crowding reagents. It is another object to provide a method for normalizing the concentration of nucleic acids of multiple nucleic acids solutions. It is yet another object to provide such reagent compositions for releasing bound nucleic acids from solid phase materials.

DETAILED DESCRIPTION OF THE INVENTION

Figure 1:
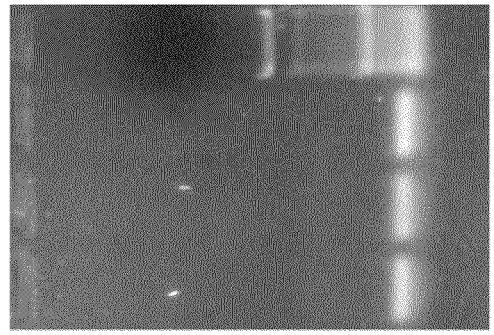
FIG. 1 is a photographic image of an agarose gel which shows isolation of DNA, from a PCR mixture.

The present invention is to provide a method for isolation and/or normalization of nucleic acids from a solution based on the discovery that nucleic acids bind non-specifically and reversibly to solid phase surfaces with multi-amide-bond functional groups at certain salt and pH conditions. The method comprises contacting the nucleic-acids-containing solution with a solid phase material with functional groups which are able to bind the nucleic acids to the material and then extracting the nucleic acids. The solid phase materials can be in the form of particles, microparticles, fibers, beads, membranes, and other supports such as test tubes and microwells, pippette tips. As a result, methods for cost-effective, convenient and rapid separation of polynucleotides such as DNA, RNA and PNA, from other molecules, such as proteins, lipids, polysaccharides, nucleotides are available. The following is a description of the present invention with reference to nucleic acids as exemplified by DNA. It is to be understood that the present invention, is also useful for separation of RNA and PNAs in a similar manner. Because when using crowding reagents, such as polyethylene glycol (PEG), ethanol and isopropanol, small polynucleotides require higher concentration of crowding reagents for binding, it is possible to manipulate the concentration of the crowding reagents to selectively promote the binding or releasing of polynucleotides on the basis of size.

One embodiment of the present invention is a method of separating DNA from a solution containing DNA. The method comprises a first step of reversibly binding DNA non-specifically to solid surface materials, such as magnetic particles whose surfaces are coated with functional groups with multiple amide bonds. The functional groups consist of preferably two consecutive amide bonds without any charge groups attached to the functional groups of the amide bonds. The structure of one example of such functional groups is shown as below. The R group can have from 1-20 carbon atoms.

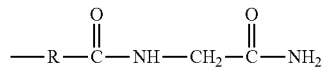

In one embodiment, the magnetic particles are combined with a solution of DNA with low ionic strength and a pH suitable for binding DNA to the solid surface of magnetic particles. The salt concentration is from 0.1 to 100 mM. The pH is from 5 to 10. As a result, DNA is bound to the surfaces of the magnetic particles. Subsequently, the magnetic particles in the resulting combination are separated from the supernatant. The magnetic particles optionally, can be washed with a suitable wash buffer before they are contacted with a suitable elution buffer, to elute and separate the DNA from the magnetic particles. In a final step, the magnetic particles are separated from the elution buffer, which contains the polynucleotides in solution. The magnetic particles are separated from elution buffer by, for example, filtration, centrifugation or applying a magnetic field.

In another embodiment, the magnetic particles are combined with a nucleic-acid-containing solution with high ionic strength and a pH suitable for binding DNA to the solid surface of magnetic particles in the presence of crowding reagents. The salt concentration is from 100 mM to 3 M. The pH is from 5 to 10. The crowding reagents include ethanol, isopropanol, polyethylene glycol (PEG) or a mixture of any of the above reagents. The concentration of the crowding reagents required for nucleic acids binding can be determined empirically by a person skilled in the art. As a result, DNA is bound to the surfaces of the magnetic particles. Subsequently, the magnetic particles in the resulting combination are separated from the supernatant. In subsequent steps, the salt and crowding reagents are removed and DNA remains bound to the magnetic particles. The magnetic particles can be washed with a suitable wash buffer to remove excess salt while maintaining the binding of nucleic acids to the magnetic particles. The magnetic particles can be optionally further washed with a suitable low ion strength buffer while maintaining the binding of nucleic acids to the magnetic particles before they are contacted with a suitable elution buffer, to elute and separate the DNA from the magnetic particles. In a final step, the magnetic particles are separated from the elution buffer, which contains the polynucleotides in solution. The magnetic particles are separated from elution buffer by, for example, filtration, centrifugation or application of a magnetic field.

In one embodiment, the PEG has an average molecular weight of about from 400 to 10,000. Preferably, the molecular weight of PEG is between 600 and 8000. In general, the concentration of PEG can be determined empirically by a person skilled in the art to achieve facilitating nucleic acid binding to solid phase. Appropriate PEG concentration (final concentration) for use in the methods of the present invention are from about 5% to 30%, preferably from 8% to 20%. Appropriate alcohol (e.g., ethanol, isopropanol) concentration (final concentration) for use in the methods of the present invention are from about 10% to 85%, preferably from 25% to 70%. PEG and alcohol may be mixed so long as allowing nucleic acid binding to amide-coated solid phase surface. In the case of mixed PEG and/or alcohol, the concentration of each component can be determined empirically by a person skilled in the art to achieve the binding of nucleic acids to the solid phase surface.

Preferably the releasing step is performed at a pH greater than 11 but less than 12 to maintain the integrity of the nucleic acids and to allow retrieval of nucleic acids. Salt, e.g., NaCl, KCl, at a concentration of less than 100 mM may be used to release nucleic acids at a pH lower than 11 at the elution step. Once the bound DNA has been eluted, the solid phase is separated from the elution buffer.

A "solid phase" is an entity that is essentially insoluble under any conditions upon which a nucleic acid can be bound. The surface of the solid phase is coated with amide functional group for reversible nucleic acid binding. The solid phase materials for binding DNA with sufficient surface area to permit efficient DNA binding can be used in the present invention. The preferred solid phase materials are silica, a plastic such as polystyrene or a magnetic or magnetizable material, and in particular gamma-iron oxide.

Any solid phase known to a person skilled in the art can be used as the solid phase such as particles, microparticles, fibers, beads, membranes, and other supports such as test tubes, microwells, pippette tips, microliter plates. Generally, magnetic particles having a diameter of $\geq 1$ nm to $\leq 1$ mm are preferably used as the solid phase which enables access to a favorable specific surface per gram particles. As used herein, "magnetic particles" are microparticles that are attracted by a magnetic field.

The magnetic microparticles used in the method of the present invention comprise a magnetic metal oxide core, which is generally surrounded by an adsorptively or covalently bound silane coat to which a wide variety of bioaffinity adsorbents can be covalently bound through selected coupling chemistries, thereby coating the surface of the microparticles with functional groups. A person skilled in the art may devise other coating method for functional group coupling.

As used herein, the term "amide functional group-coated surface" or a similar phrase refers to a surface which is coated with moieties which each has free amide functional group which is bound to the amino silane on the microparticle; as a result, the surfaces of the microparticles are coated with the amide-functional-group-containing moieties. Two or more amide bonds in each moiety of functional groups are used as the bioaffinity adsorbents in the current invention. The functional group containing multi-amide bonds acts as a bioaffinity absorbent for nucleic acid in solution. The number of amide bonds in the functional group necessary for reversible nucleic acid binding can be determined by a person skilled in the art using no more than routine experimentation. In one embodiment, the multi-amide functional group has two amide bonds (double-amide group). The double-amide group-coated magnetic microparticles are commercially available from Aline Biosciences (Magabind-1, Catalog number M-1001-2). Other non-charged multi-amide functional group may be used to coat the solid phase surface by a person skilled in the art using no more than routine experimentation.

"Non-specific binding" refers to the binding of different nucleic acid molecules without differentiation of the particular sequence of the nucleic acids. "A solution containing nucleic acid" can be any aqueous solution, such as solution containing DNA, RNA and/or PNAs. Such a solution can also contain other components, such as other biomolecules, inorganic compounds and organic compounds. The solution can also be a cleared lysate. A "lysate" is a solution resulting from disrupted cells containing DNA and/or RNA. A "nucleic acid crowding reagent" is a composition that causes a nucleic acid molecule to go out of solution. Suitable crowding reagents include alcohols, e.g., ethanol or isopropanol and PEG.

The temperature does not appear to be critical in the method of isolating DNA of the present invention. Any temperature above freezing point of water and below the boiling point of water can be used. Ambient temperature is preferred.

The pH can be formulated in the range of pH 3.0-11.0 for nucleic acid binding to an amide-functional-group-coated solid phase surface. Preferably, pH 6.0-9.0 is used.

In a preferred embodiment, the isolated nucleic acid of one or a plurality of samples is subjected to further analysis, e.g., polymerase chain reaction (PCR).

As used herein the term "separating" or "isolating" is intended to mean that the material has been completely, substantially or partially separated, isolated or purified from other components, e.g., membrane, proteins.

General Methodology

The magnetic particles used in the following examples were the double-amide coated magnetic microparticles from Aline biosciences, Massachusetts, (Magbind-1, M-1001-5). The particles were 1 micron meter in diameter. The particles were stored in Tris-HCl buffer at a concentration of 50 mg/mL. All agarose gels were run using 0.8-1.5% final agarose with 1X TAE buffers. The gels were post-stained with ethidium bromide and visualized under UV.

EXAMPLES

Example 1 dsDNA Isolation and Purification from PCR Product

Magnetic particles which have amide functional groups on their surface were prepared in a solution containing 10% magnetic beads by weight, 10 mM TrisHCl, pH 7. The samples to be examined were placed in a 96-well microtiter plate. 10 ul of PCR product was mixed with 10 ul of the solution containing magnetic particles, mixed and incubated at room temperature for 5 min.

The microtiter plate containing the samples was subsequently placed for 1 minute in a magnetic holder, the supernatant was discarded and the particles were washed once with 150 ul of de-ionized water.

Finally the microtiter plate was removed from the magnetic holder and the particles were resuspended in a 20 ul of elution buffer (10 mM NaOH) and incubated for 1 min. The mictiter plate was again placed in the magnetic holder and the eluate was removed after 1 min.

Results: Loaded 18 ul of DNA-containing eluate from each sample on an agraose gel. As shown in FIG. 1, the methods described herein can be used to purify DNA from a solution.

Example 2

DNA Purification and Normalization from PCR Product

Magnetic particles which have amide functional groups on their surface were prepared in a solution containing 0.5% magnetic beads, 10 mM TrisHCl, pH 7.5

1. 5 ul, 10 ul, 15 ul, 20 ul of PCR product were added into each well separately in a 96-well microtiter plate.

2. 10 mM TrisHCl, pH 7.5 was added into each well to bring the final sample volume to 35 ul resulting in different concentrations between samples.

3. 5 ul of magnetic bead solution was added into each well containing PCR product, mixed and incubated at room temperature for 5 min.

4. The microliter plate containing the samples was subsequently placed for 1 minute in a magnetic holder.

5. The supernatant was discarded and the particles were washed once with 100 ul of de-ionized water on magnet.

6. The microliter plate was removed from the magnet and the particles were resuspended in a 20 ul of elution buffer (10 mM NaOH) and incubated for 1 min.

7. The microtiter plate was placed in the magnet and the eluate was removed after 1 min.

Figure 2:
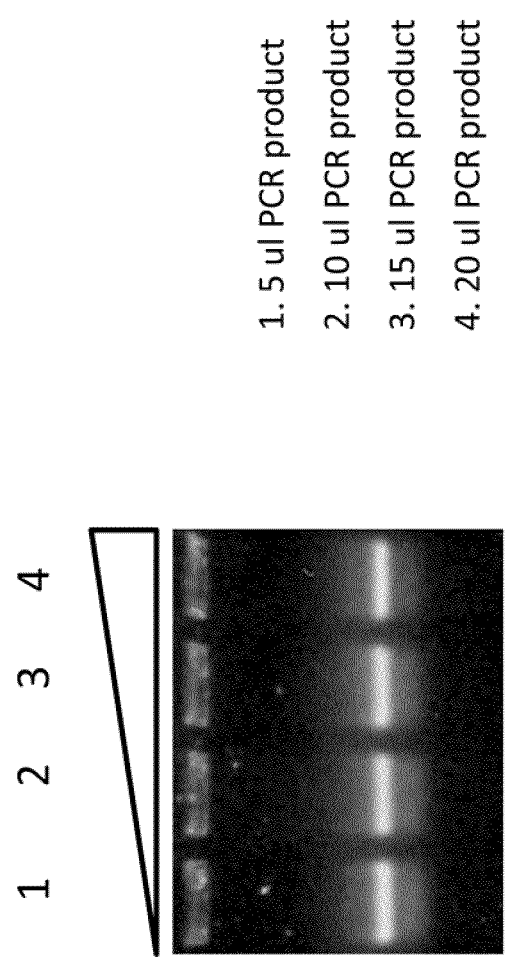
FIG. 2 is a photographic image of an agarose gel which shows the purification and normalization of PCR product.

Results: Loaded 18 ul of purified DNA from each sample on an agarose gel. As shown in FIG. 2, despite the initial difference in concentration of different samples, the purified DNA samples had similar concentrations. The methods described herein can be used to purify and normalize DNA.

Example 3

Genomic DNA Isolation from Human Blood

1. Aliquoted 200 ul human blood into 1.5 mL Eppendorf tubes.

2. Added 2 volumes of lysis buffer (0.5% SDS, 1% Triton X-100, 30 mM EDTA, 20 mM TrisHCl, pH 7.8) and 10 ul of proteinase K and gently mixed 5 times.

3. Incubated at 37 C for 10 minutes.

4. Added 0.5 volume of binding buffer (40% PEG1000, 1.5 M NaCl, 0.2% solids magnetic beads) and gently mixed 10 times.

5. Placed on magnet holder for 10 minutes,

6. Removed supernatant and discarded.

7. Resuspended beads in 800 ul of wash buffer (6 M urea, 14% PEG 1000, 1 M NaCl) off magnet.

8. Placed on magnet holder for 10 minutes,

9. Discarded supernatant—repeated steps 7 and 8 for a second wash.

10. Washed beads once with 500 ul 70% ethanol, without disturbing the beads.

11. Washed beads twice with 500 ul of de-ionized water, without disturbing the beads.

12. Resuspended beads off magnet in 100 ul of NaOH and sat on bench for 1 minute.

13. Placed on magnet for 2 minutes.

14. Transferred DNA containing superanant to clean wells for storage.

Figure 3:
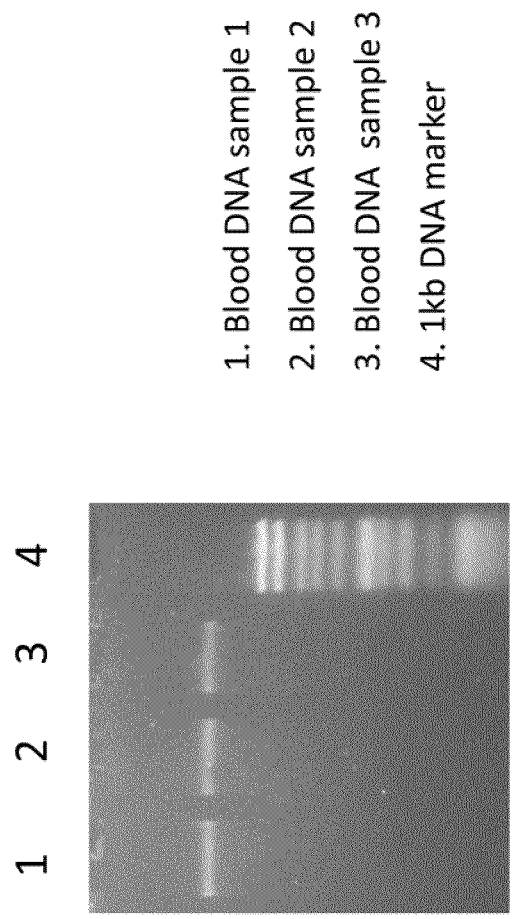
FIG. 3 is a photographic image of an agarose gel which shows the separation of genomic DNA from blood samples.

Results: Loaded 2 ul of DNA from each sample on an agarose gel. As shown in FIG. 3, the methods described herein can be used to isolate genomic DNA from whole human blood.

EQUIVALENTS

While the foregoing invention has been described in some detail for purposes of clarity and understanding, it will be ascertain to one skilled in the art using no more than routine experimentation, from reading of this disclosure that various changes in form and detail can be made without departing from the true scope of the invention. For example, all the techniques and apparatus described above can be used in various combinations. Such changes are considered to be equivalents and intended to be encompassed in the scope of the following claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of reversibly binding nucleic acids non-specifically to a solid phase material having a surface coated with one or more functional groups with multiple amide bonds without relying on any crowding reagent, the method comprising the steps of:
   a) contacting a surface of a solid phase material coated with one or more functional groups with multiple amide bonds with a solution containing nucleic acids; and
   b) adjusting the salt concentration and pH of the solution until suitable for binding the nucleic acids onto the surface of the solid phase material, thereby binding the nucleic acids non-specifically to the one or more functional groups with multiple amide bonds and therefore the solid phase material without relying on any crowding agent.

2. The method of claim 1, wherein the salt is selected from the group consisting of sodium chloride, magnesium chloride, potassium chloride, sodium sulfate, magnesium sulfate, potassium sulfate, sodium phosphate, potassium phosphate, sodium nitrate, and potassium nitrate.

3. The method of claim 1, wherein the pH is adjusted to between 4 and 11.

4. The method of claim 1, wherein the pH is adjusted to between 6 and 9.

5. The method of claim 1, wherein the nucleic acids bound to the solid phase material are subsequently released from the solid phase material by dissolving the nucleic acids in an elution solution.

6. The method of claim 5 wherein the elution solution is a solution with pH greater than or equal to 11.

7. The method of claim 5, wherein the elution solution is a salt solution.

8. The method of claim 7, wherein the salt in the elution solution is selected from the group consisting of sodium chloride, magnesium chloride, potassium chloride, sodium sulfate, magnesium sulfate, and potassium sulfate.

9. The method of claim 7 in the elution solution, wherein the salt concentration is greater than 100 mM.

10. The method of claim 1, wherein the nucleic acid-containing solution is the result of an enzyme reaction.

11. The method of claim 10, wherein the enzyme is selected from the group consisting of polymerase, ligase, polynucleotide kinase, reverse transcriptase and restriction enzymes.

12. The method of claim 1, wherein the nucleic acid-containing solution is the result of lysed cells, tissue, or bodily fluid.

13. The method of claim 1, wherein the nucleic acid-containing solution is a purified solution.

14. A method of separating nucleic acids from a solution containing nucleic acids, comprising the steps of:
   a) combining a solid phase material surface-coated with one or more functional groups with multiple amide bonds and a solution containing nucleic acids, thereby producing a first combination;
   b) adjusting the salt concentration of the first combination until suitable for binding nucleic acids to the surface of the solid phase material, thereby producing a second combination comprising nucleic acids bound non-specifically to the one or more functional groups with multiple amide bonds and therefore the solid phase material without relying on any crowding agent;
   c) separating the solid phase material from the second combination;
   d) contacting the solid phase material separated in c) with the bound nucleic acids in an elution solution, whereby nucleic acids separate from the solid phase material and dissolve into the elution solution; and
   e) separating the solid phase material from the elution solution.

15. The method of claim 14, further comprising a step of washing the solid phase material with a wash buffer solution wherein the wash buffer solution dissolves impurities bound to the solid phase material while leaving the DNA bound to the solid phase material.

16. The method of claim 14, wherein elution solution comprises one or more crowding reagents, wherein the concentration of the one or more crowding reagents is selected such that the elution solution dissolves small nucleic acid fragments bound to the solid phase materials while leaving large nucleic acid fragments bound to the solid phase material.

17. The method of claim 14 wherein the elution solution is a solution with pH above 11.

18. The method of claim 14, wherein the elution solution is a salt solution.

19. The method of claim 18, wherein the salt concentration in the elution solution is above 100 mM.

20. The method of claim 14, wherein the nucleic acids-containing solution comprises the product of enzyme reaction.

21. The method of claim 20, wherein the enzyme is selected from the group consisting of polymerase, ligase, polynucleotide kinase, reverse transcriptase and restriction enzymes.

22. The method of claim 14, wherein the nucleic acids-containing solution is a purified solution.

23. The method of claim 1 wherein the multiple amide bonds comprises two consecutive amide bonds.

24. The method of claim 1 wherein the one or more functional groups have no charge groups attached thereto.

25. The method of claim 1 wherein the one or more functional groups is represented by a general formula as follows:

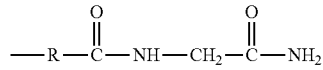

wherein the R group has 1-20 carbons.

26. The method of claim 1 wherein the solid phase material is selected from the group consisting of silica, plastic, and magnetic or magnetizable material.

27. The method of claim 1 wherein the solid phase material is a microparticle comprising a magnetic metal oxide core.

* * * * *